United States Patent [19]
Ellis

[11] Patent Number: 5,147,367
[45] Date of Patent: Sep. 15, 1992

[54] DRILL PIN GUIDE AND METHOD FOR ORTHOPEDIC SURGERY

[76] Inventor: Alfred B. Ellis, 5263 Santa Elena, El Paso, Tex. 79932

[21] Appl. No.: 660,719

[22] Filed: Feb. 22, 1991

[51] Int. Cl.⁵ .................... A61B 17/56; A61B 17/58
[52] U.S. Cl. ................................ 606/96; 606/60; 606/73
[58] Field of Search ................... 606/96–98, 606/72, 73, 60

[56] References Cited

U.S. PATENT DOCUMENTS

| | | | |
|---|---|---|---|
| 2,143,922 | 1/1939 | Longfellow | 606/73 X |
| 2,200,120 | 5/1940 | Nauth | 606/96 |
| 2,500,370 | 3/1950 | McKibbin | 606/96 X |
| 4,037,592 | 7/1977 | Kronner | 606/96 |
| 4,360,012 | 11/1982 | McHarrie et al. | 606/54 |
| 4,383,527 | 5/1983 | Asnis et al. | 606/96 |
| 4,450,835 | 5/1984 | Asnis et al. | 606/96 X |
| 4,465,065 | 8/1984 | Gotfried | 606/96 X |
| 4,570,624 | 2/1986 | Wu | 606/96 |
| 4,608,972 | 10/1986 | Small | 606/96 |
| 4,672,957 | 6/1987 | Hourahane | 606/96 |
| 4,713,077 | 12/1987 | Small | 606/96 X |
| 4,719,907 | 11/1988 | Banko et al. | 606/96 |
| 4,754,749 | 7/1988 | Tsou | 606/73 |
| 4,848,327 | 7/1989 | Perdue | 606/96 |

Primary Examiner—Robert A. Hafer
Assistant Examiner—Kevin G. Rooney
Attorney, Agent, or Firm—Baker & Botts

[57] ABSTRACT

A drill pin guide and method is disclosed for the fixation of bone fractures. A surgeon first inserts a small orthopedic pin through a bone fragment into the underlying bone mass to stabilize the fracture. Next a drill guide is placed over a portion of the pin protruding from the bone and is used to position a drill bit for drilling a small hole parallel to the inserted pin. After removing the drill pin guide a surgical screw is inserted into the drilled hole. By properly adjusting the distance between pin and screw, the surgeon may create an interference fit between the two thus preventing either from unintentionally loosening.

17 Claims, 2 Drawing Sheets

DRILL PIN GUIDE AND METHOD FOR ORTHOPEDIC SURGERY

TECHNICAL FIELD

The present invention is directed to an apparatus and method of setting bone fragments relative to the adjacent bone mass.

BACKGROUND OF THE INVENTION

Surgical screws and pins used in the fixation of bone fractures and separations occurring in humans and in animals are well known in the art. The medical devices and methods known heretofore, however, are poorly suited for treating fractures and separations of small bones or for treating those fractures and separations resulting in small bone fragments. These types of injuries require more than a simple downsizing of existing equipment.

A common problem encountered when two or more bones are to be joined together after a break or fracture is that they must be positioned properly relative to each other. The surgeon accomplishes this by first maneuvering the bones into the relative position he or she believes to be proper and then inserts a first pin or screw. If the bones are not positioned properly the pin (or screw) must be removed and a new hole drilled. This second hole is close to the first, particularly in small bones, and thus often slips because the hole in the bone is elongated. Thus, often it is necessary to position a second hole very close to a first hole without the two holes overlapping and with the holes having a fixed and measurable positional relationship with each other.

A second problem is that when a pin is used for the initial stabilization it is often necessary to lock that pin in place such that at a future time the pin can be easily removable.

One such device is disclosed in U.S. Pat. No. 4,360,012 to McHarrie et al. This prior art discloses a large orthopedic fixture for drilling parallel bores through a long straight bone. A guide is attached to a elongate member and allows a drill bit to be aligned along a known direction. The guide may be repositioned along the elongate member to create other holes. The size of the device makes it particularly ill-suited for the repair of small bone breaks. Small bone fragments are often smaller than the disclosed guide itself. Also, the device does not address how the fractured bone is temporarily held in place while the first bore is drilled. Maintaining the desired alignment between the bone fragment and the underlying bone mass while drilling a hole in a surgical setting can be difficult, to say the least.

U.S. Pat. No. 4,037,592 to Kronner discloses a guide pin locating tool and method. The disclosed device is intended for use in repairing a separation of the femoral shank from the femur. The tool is temporarily attached to the base of the femur with a pin inserted into the bone. A drill guide is attached to the base and pivots in two axes for precise alignment prior to drilling. Again, this prior art does not lend itself generally to small bone breaks. The guide is large and requires a large surgical incision along the femur to accommodate its use. The guide requires the insertion of a pin (for attachment of the base) that ultimately does not strengthen the break. The tool also fails to provide a means for preventing the bone fragment from rotating about the axis containing the inserted pin. A bone fragment may spin about a single pin if the fracture occurs predominantly along a single plane.

U.S. Pat. No. 4,608,972 to Small discloses a method of applying a chin implant, drill guide tool and implant. This prior art attaches a chin implant to the human mandible with two screws. The screws are laterally spaced by two channels within the guide. The device itself is aligned on the jaw with a third channel by a temporary pin inserted into the jaw. Although this device provides positive counter-rotational means, it does so at the expense of size, inflexibility and complexity. The guide uses two relatively large screws separated by an invariable distance positioned by an alignment pin that is immediately removed and discarded. The method is not suited to growing bones. In such circumstances, bone growth under the had of each screw would damage the growth of the bone.

U.S. Pat. No. 4,754,749 to Tsou discloses a surgical screw with counter-rotation prevention means. Here a surgical pin is inserted through a channel machined into the head of the installed screw nd into the underlying bone mass. The screw and pin form an acute angle. The disclosed device does not indicate how the screw is initially aligned relative to the bone nor how the alignment is maintained during drilling of the hole.

Therefore, a need has arisen in the art for a drill guide and method that is suitable for the repair of small bone breaks and which provides a positive means for aligning the bone piece and underlying bone mass during drilling.

A further need exists in the art for such a guide having a counter-rotational means to prevent the bone fragment and screw from rotating relative to the underling bone mass.

A still further need exists in the art for such a guide that is adaptable to fractures or separation in growing bones.

A still further need exists in the art for bone stabilization method and device which allows for holes to be drilled parallel to each other and in close proximity to each other.

A still further needs exists in the art for such a device and method which allows for multiple holes to be drilled in a bone, all spaced in relative close proximation to each other and all having a controlled angle of bone penetration.

A still further need exists in the art for a device and method of bone stabilization which allows for the selective locking and releasing of adjacent stabilizing pins.

SUMMARY OF THE INVENTION

In accordance with the present invention, a drill guide is provided which substantially solves or reduces disadvantages and problems associated with prior drill guides.

A drill pin guide is provided for installing an interlocking pin and screw through a bone fragment and into the underlying bone mass. More specifically the drill guide allows a surgeon to drill a second hole adjacent to a first pin hole through a bone piece and into the adjacent bone mass while maintaining positive alignment of the two bone pieces. An interference fit is created between the pin and screw to prevent both from moving once installed.

The guide advantageously can be a cylinder having a depth wide enough to control the angle of attack of the hole with respect to the bone. Two holes, or channels, are constructed through the longitudinal axis of the guide parallel (at least in one embodiment) to each other.

A first pin is inserted through one bone and into the bone mass to initially position and stabilize the bone pieces. The end of the pin is allowed to protrude from the bone. One hole of the guide is used to slip the guide over the exposed pin end thereby positioning the guide against the bone to stabilize the guide. A drill bit is placed through the second parallel hole and is used to bore through the bones to create a screw hole in the bones. The guide and drill bit are removed and a screw is placed into the second hole. The head of the screw contacts the pin and prevents the pin from moving outward. A second pin may be instead inserted into the bone pieces through the drill bit channel.

The guide is suitable for installing multiple pins.

One technical advantage of the disclosed device is its suitability for use in the repair of small bone breaks.

A second technical advantage is the device's ability to maintain alignment between a bone fragment and its underlining bone mass while a drill bit is used to bore a hole for receiving a screw.

Another technical advantage is the ability of the device and method to create an interference fit between an inserted screw and pin. The two are thereby prevented from subsequent motion, yet are removable by a surgeon at a later date if desired.

A fourth technical advantage of the disclosed invention is its ability to resist movement of the bone fragment in all directions of motion during the patient's recovery. The threads of the screw prevent the bone fragment and bone mass from separating along the axis of the screw or from sliding in the plane perpendicular to the screw. The combined effect of the pin and screw stop the bone fragment from rotating about either the pin or screw.

A still further technical advantage of the device is its ability to insert multiple pins into or guide multiple drill bits through the bone fragment and into the underlining bone mass at precise locations if desired. The use of multiple pins can be advantageous for the repair of particularly small bone fractures and in bones still subject to growth.

BRIEF DESCRIPTION OF THE DRAWINGS

For a more complete understanding of the present invention and the advantages thereof reference is now made to the following descriptions taken in conjunction with the accompanying diagrams in which.

DETAILED DESCRIPTION OF THE INVENTION

Figure 1:
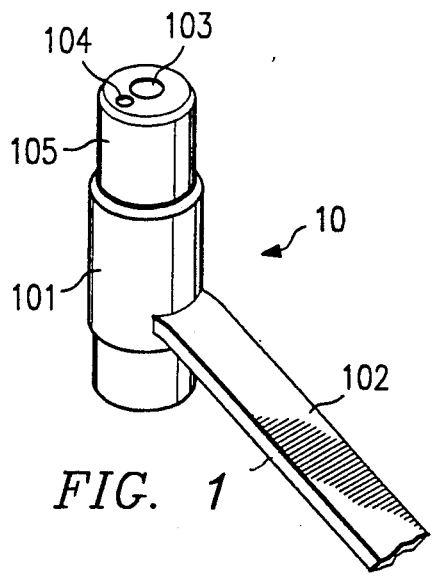
FIG. 1 depicts one embodiment of the disclosed drill guide.

FIG. 1 depicts a drill pin guide 10 embodying the disclosed invention. Drill pin guide 10 consists of a body 101 and a handle 102. Body 101 contains channels 103 and 104. Channel 104 is sized to accept an orthopedic pin, typically of diameter 0.035, 0.045, 0.062 or 0.078 inches. Channel 103 is sized to accept, in one embodiment, a drill bit, and, in another embodiment, a second orthopedic pin. Typically, channel 103 would accept a drill bit for screws of diameter 2.7, 3.0, 3.5 or 4.5 mm or a pin again of diameter 0.035, 0.045, 0.062 or 0.078 inches. Channels 103 and 104 are parallel and fully pierce body 101. Channels 103 and 104 are further laterally spaced from one another to create an interference fit between pin and screw as described more fully below. Body 101 may contain an inner barrel 105 containing channels 103 and 104 rotatable relative to the outside surface of body 101. This feature facilitates the universal placement of channels 103 and 104 with respect to handle 102.

Figure 2B:
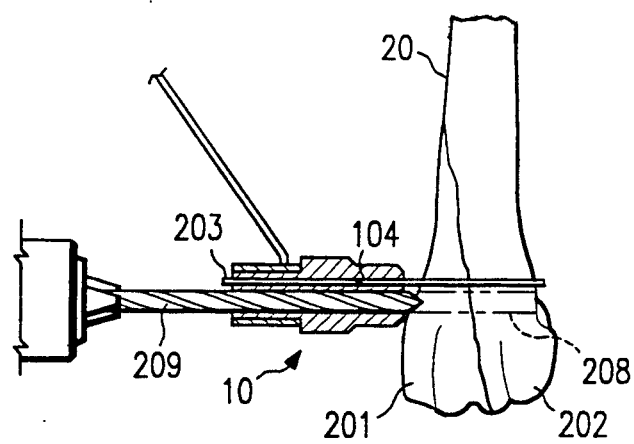
FIGS. 2a, 2b, 2c and 2d depict the disclosed method of inserting an interlocking pin and screw in connection with the disclosed drill guide.
Figure 2C:
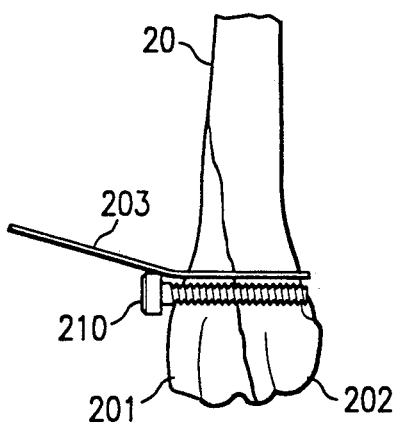
Figure 2A:
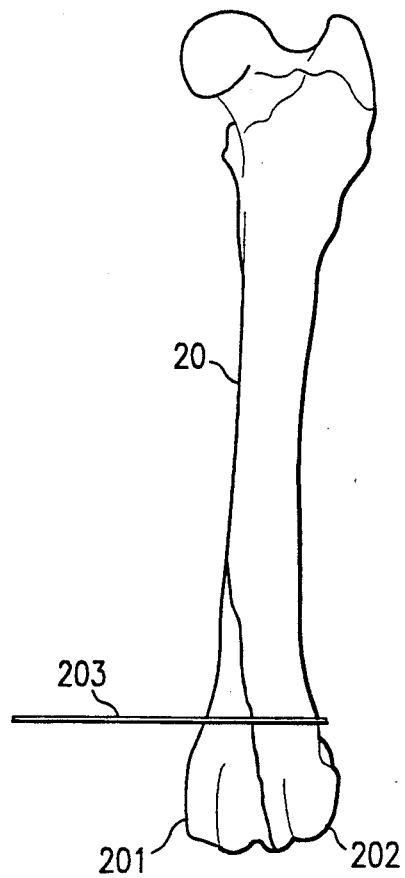

FIG. 2a depicts a femur 20 which contains a fractured condyle 201 and an adjacent underlying bone mass 202. Although the present invention is depicted in conjunction with a medial condyle fracture of the femur, the disclosed drill pin guide is suitable for the repair of a wide range of fractures or separations in humans as well as in animals. In particular, drill pin guide 10 is well suited in conjunction with sacroiliac luxations, condylar "T" and "Y" fractures of the humerus and femur, femoral neck fractures and in jaw fractures.

Typically a surgeon would insert pin 203 through bone fragment 201 and into underlying bone mass 202. The surgeon leaves a portion of pin 203 protruding from at least one side of both bone pieces. Here, pin 203 protrudes from bone fragment 201. Pin 203 is small enough that it may be inserted manually without first drilling a hole by the surgeon who simultaneously aligns bone fragment 201 with bone mass 202. Pin 203 is inserted along a line determined by the surgeon in light of the present discussion. Pin 203 may be bent (not shown) where it emerges from the bone at this point to select a different path for channel 103 as discussed more fully below. The surgeon may choose to do so to adjust the final placement of the adjacent screw or to provide additional rigidity to the bone fragment as described in connection with FIG. 4.

In FIG. 2b, drill pin guide 10 is inserted onto the portion of pin 203 protruding from bone 20. Pin 203 passes through all or part of channel 104 depending upon its exposed length. Once the surgeon has stabilized the fracture with pin 203 he next bores socket 208 with drill bit 209 which passes through channel 103 of guide 10. Hole 208 parallels the portion of pin 203 protruding from bone fragment 203 because channels 103 and 104 are parallel to one another. Advantageously, channel 103 is at the center of guide 10 to prevent rotation of the guide during drilling.

After drilling hole 208, the surgeon removes drill guide 10 as in FIG. 2c. A standard orthopedic screw 210 is then inserted into hole 208 to join bone fragment 201 with bone mass 202. Channels 103 and 104 are spaced to provide an interference fit between screw 210 and pin 203. Specifically the head of pin 210 is larger in diameter than the shaft such that it comes into contact with pin 203 causing an interference fit. Pin 203 can then be cut to its desired size.

For example, if pin 203 is 0.062 inches in diameter and if the screw 210 has a shaft diameter of 3.0 mm and a head diameter of 6.0 mm, then the screw and pin channels must be separated by 3.0 mm (center of pin to center of screw) to create the desired interference fit. A 2.7 mm drill bit is typically used to bore the socket for a 3.0 mm screw.

Figure 2D:
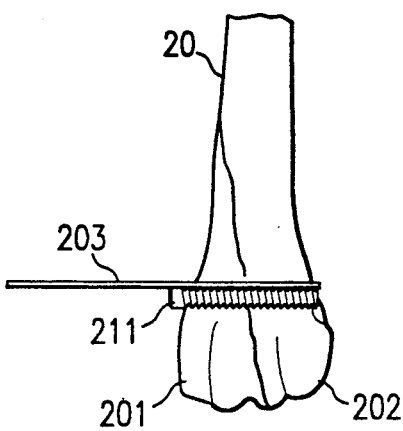

FIG. 2d depicts a second embodiment of the disclosed pin guide. Here screw 211 tangentially contacts the body of pin 203.

Both of the above interference fits prevent the screw and pin from loosening or from moving. A surgeon, however, can, remove the screw and pin if desired once the bone is healed. The screw is simply unscrewed with a screwdriver using a moderate amount of force and the pin is extracted with forceps or pliers.

Figure 3:
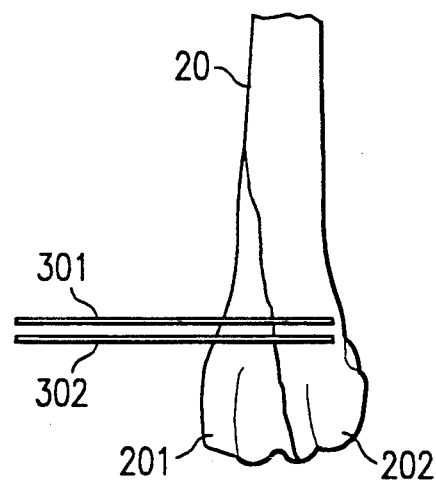
FIG. 3 depicts a second embodiment of the disclosed method employing multiple parallel pins.

FIG. 3 depicts another embodiment of the disclosed method. Here bone 20 is repaired with pins 301 and 302. Pin 301 is installed as described above in connection with FIG. 2a. Pin 302 is inserted parallel to pin 301 with the aid of channel 104 of drill guide 10 (not shown).

In a similar manner any number of pins or screws may be inserted into bone 20 along parallel lines by moving drill guide 10 from one pin to the next and inserting an additional pin. The spatial pattern of pins can be completely controlled by the surgeon who has several drill pin guides, each with a slightly different screw center to pin center distance.

The method described in FIG. 3 is particularly suited when bone fragment 201 is too small to support a single screw or when the fractured bone is still growing. Growing bones cannot accommodate screws with heads since the heads cause additional damage to the bone as the bone grows and compresses against the screw head.

A surgeon may also insert multiple pins in an attempt to identify the optimum pin or screw pathway. In such a case, a final pin or screw would be inserted using previous insertions as approximations and all unnecessary pins removed. Since the distance between channels on the guide is known, precise placement is possible. A surgeon may also use an x-ray or fluoroscope to help identify the best pathway during surgery. A pin can again be used as an intermediate reference pathway.

Figure 4:
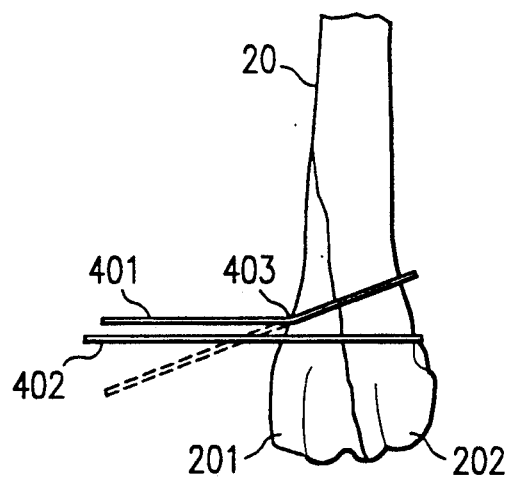
FIG. 4 depicts a second embodiment of the disclosed invention employing multiple nonparallel pins.

FIG. 4 shows a third embodiment of the disclosed method. In FIG. 4 a bone fragment 201 may be secured to bone mass 202 of bone 20 in a manner very resistant to subsequent motion using drill pin guide 10 (not shown). A first pin 401 is inserted into bone fragment 201 as described in connection with pin 203 of FIG. 2a. Pin 401 is then bent at the base of bone fragment 201 at point 403. Use of the drill guide as described in connection with FIG. 3 then produces the nonparallel path depicted by pin 402. This method is particularly suited to repairs where bone fragment 201 is too small to allow placement of a single screw yet where it is desirous that bone fragment 201 be held more securely to bone mass 202 than is possible with multiple parallel pins. Nonparallel pins 401 and 402 lock bone fragment 201 to bone mass 202 by virtue of their divergence (or convergence).

Figure 5:
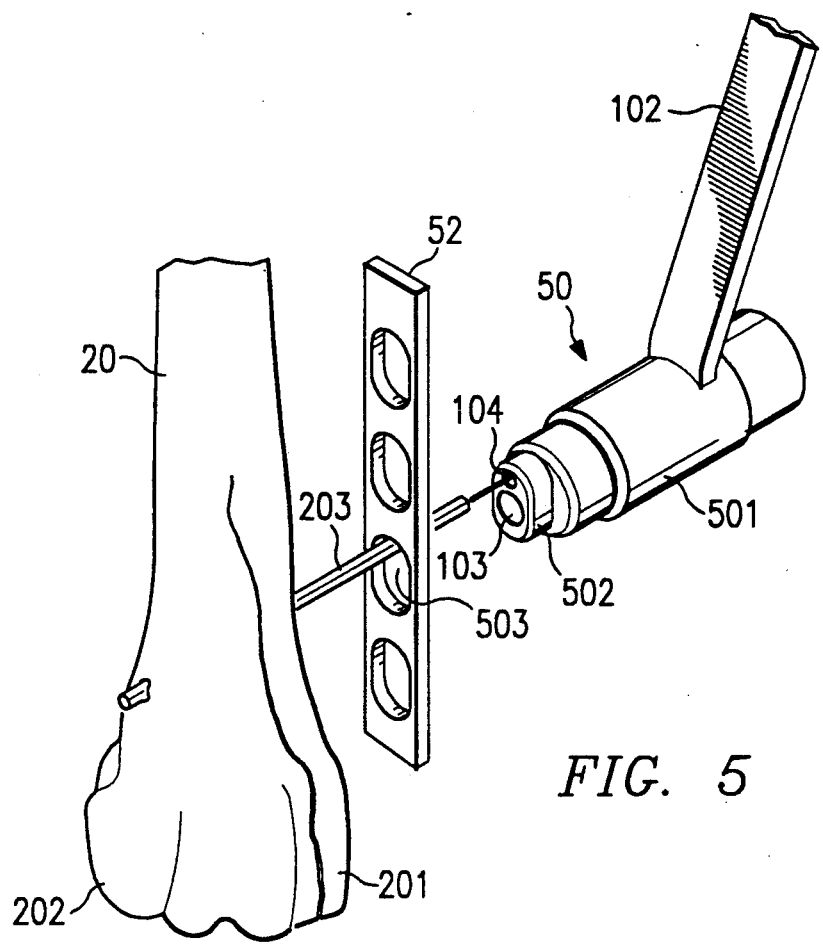
FIG. 5 depicts the disclosed invention used in connection with a standard compression bone plate or omniplate.

FIG. 5 depicts how the disclosed drill pin guide can be adapted for use with a standard compression bone plate or omniplate 52. Channels 103 and 104 are machined into body 501 of drill guide 50. Body 501 contains a nipple 502 which mates with hole 503 of bone plate 52. Pin 203 is inserted into bone 20. A hole is then bored using drill guide 50 as described in connection with FIG. 2b. This procedure allows a bone plate to be used where size, alignment and stability problems might otherwise preclude its use.

Although the present invention has been described in detail, it should be understood that various changes, substitutions and alterations can be made hereto without departing from the spirit and scope of the invention as defined by the appended claims. For example, one or both of the channels can be other than round to accommodate special fastening devices having oblong, rectangular or square elongated members.

What is claimed is:

1. An orthopedic device for setting a bond fragment relative to an adjacent bone mass, said device comprising:
    a body;
    a barrel located on and rotatable relative to said body;
    a first channel through said barrel for accepting a first elongated orthopedic fastening device installed in said bone fragment and for aligning said barrel along said first elongated orthopedic fastening device; and
    a second channel for laterally spacing a second elongated fastening device from said first elongated orthopedic fastening device and for aligning said second elongated orthopedic fastening device parallel to said first elongated orthopedic fastening device.

2. The orthopedic device of claim 1 wherein said second channel is sized for accepting a drill bit for boring a socket through said bone fragment and into an adjacent bone mass, said socket for accepting said second device.

3. The orthopedic device of claim 1 wherein an interference fit is created between said first device and said second device preventing movement of said first device out of said bone fragment and mass when both said devices are installed in said bone fragment and mass.

4. The device of claim 3 wherein said first device is an orthopedic pin and said second device is an orthopedic screw.

5. The device of claim 1 wherein said body is cylindrical.

6. The device of claim 5 wherein said first hole is offset from the longitudinal center line of said body.

7. The device of claim 6 wherein said second hole is along said longitudinal center line.

8. A drill pin guide for installing an interlocking pin and screw through a bone fragment and into the underlying bone mass, said guide comprising:
    a body;
    a barrel located on and rotatable relative to said body;
    a first channel through said barrel for accepting a pin installed in said bone fragments; and
    a second channel through said barrel for accepting a drill bit, for boring a socket through a bond fragment and into an adjacent bone mass; the socket for accepting a screw, said second channel aligned parallel to said first channel and laterally separated from said first channel whereby said screw contacts said pin to prevent outward movement of said pin crating an interference fit between said pin and said screw when said pin and screw are installed.

9. The method of joining two pieces of bone to form a rigid structure comprising the steps of:
    inserting a pin through a first bone piece and into a second bone piece, at least one end of the pin protruding from said first bone piece
    drilling a hole through the first bone piece and into the second bone piece, the hole being parallel to the portion of the pin protruding from said first bone piece;

installing a screw in the hole; and creating an interference fit between the screw and the pin.

10. The method of claim 9 wherein the screw has a head and a shaft, the diameter of the head being greater than the diameter of the shaft and whereby the head tangentially contacts the pin causing the interference fit.

11. The method of claim 10 further comprising the step of bending the pin at the base of the bone before said drilling step.

12. The method of claim 9 wherein at least one of the threads of the screw tangentially contacts the pin causing the interference fit.

13. The method of joining two pieces of bone to form a rigid structure comprising the steps of:

inserting a pin through a first bone piece and into a second bone piece, at least one end of the pin protruding from said first bone piece;

drilling a hole through the first bone piece and into the second bone piece, the hole being parallel to the portion of the pin protruding from si first bone piece; an installing a screw in the hole, the screw having a head larger than its shaft, the head creating an interference fit with the portion of the pin protruding from said first bone piece.

14. The method of claim 13 further comprising the step of bending the pin at the base of the bone before said drilling step.

15. The method of claim 13 further comprising the step of placing a guide over the pin before said drilling step, the guide having a first channel for receiving the pin and a second channel for receiving a drill bit, the channels being parallel to each other.

16. The method of joining two pieces of bone to form a rigid structure comprising the steps of: p1 inserting a first pin through a first bone piece and into a second bone piece, at least one end of the pin protruding from said first bone piece; p1 inserting a second pin through the first bone piece and into the second bone piece along a path parallel to the first portion of the first pin protruding from said first bone piece; p1 drilling a hole parallel to one of the first and second pins through the firs bone piece and into the second bone piece; p1 installing a screw in the hole; and p1 creating an interference fit between said one of the first and second pins and the screw.

17. A hole guide for using and stabilizing fractured bones, where such stabilization occurs as a result of a combination of one pin and one or more pins or screws inserted into at least one of said bones, said guide comprising:

a body;

a barrel having a width and thickness located on and rotatable relative to said body;

a first hole through said barrel, said first hole parallel to the axis of said thickness, said hold having a diameter corresponding to the diameter of a first pin used for insertion in at least one of said bones; and a second hole through said barrel, said second hole displaced from said first hole a fixed amount, said second hole substantially parallel to said first hole, said second hole having a diameter corresponding to the diameter of a bit used to construct a hole into at least one of said bones a fixed distance away from said pin.

* * * * *

UNITED STATES PATENT AND TRADEMARK OFFICE
CERTIFICATE OF CORRECTION

PATENT NO. : 5,147,367
DATED : September 15, 1992
INVENTOR(S) : Alfred B. Ellis

It is certified that error appears in the above-identified patent and that said Letters Patent is hereby corrected as shown below:

Column 1, line 5, after "FIELD" insert -- OF THE INVENTION --.

Column 2, line 16, after "the" delete "had" and insert -- head --.

Column 2, line 21, after "screw" delete "nd" and insert -- and --.

Column 2, line 33, after "the" delete "underling" and insert -- underlying --.

Column 2, line 38, after "for" insert -- a --.

Claim 8, Column 6, line 57, delete "crating" and insert -- creating --.

Claim 9, Column 6, line 64, after "piece" insert -- ; --.

Claim 13, Column 7, line 21, after "from" delete "si" and insert -- said --.

Claim 13, Column 7, line 22, delete "an" and insert -- and --.

UNITED STATES PATENT AND TRADEMARK OFFICE
CERTIFICATE OF CORRECTION

PATENT NO. : 5,147,367
DATED : September 15, 1992
INVENTOR(S) : Alfred B. Ellis

It is certified that error appears in the above-identified patent and that said Letters Patent is hereby corrected as shown below:

Claim 16, Column 8, line 2, delete "p1" and indent "inserting" on the next line.

Claim 16, Column 8, line 5, delete "p1" and indent "inserting" on the next line.

Claim 16, Column 8, line 8, delete "p1" and indent "drilling" on the next line.

Claim 16, Column 8. line 10, delete "firs" and insert -- first --.

Claim 16, Column 8, line 10, delete "p1" and indent "installing" on the next line.

Claim 16, Column 8, line 11, delete "p1" and indent "creating" on the next line.

Signed and Sealed this

Twenty-eighth Day of December, 1993

Attest:

BRUCE LEHMAN

*Attesting Officer*          *Commissioner of Patents and Trademarks*